(12) United States Patent
Gaertner et al.

(10) Patent No.: US 7,641,155 B2
(45) Date of Patent: Jan. 5, 2010

(54) ARRANGEMENT AND METHOD FOR AT LEAST PARTIALLY COMPENSATING A TORQUE CAUSED BY GRAVITATIONAL FORCES ACTING ON A MASS BODY

(75) Inventors: Hartmut Gaertner, Oberkochen (DE); Fritz Zimmermann, Essingen (DE); Wolfgang Strauss, Staig (DE)

(73) Assignee: Carl-Zeiss-Stiftung, Oberkochen (DE)

( * ) Notice: Subject to any disclaimer, the term of this patent is extended or adjusted under 35 U.S.C. 154(b) by 0 days.

(21) Appl. No.: 10/298,554

(22) Filed: Nov. 19, 2002

(65) Prior Publication Data

US 2003/0094549 A1 May 22, 2003

(30) Foreign Application Priority Data

Nov. 19, 2001 (DE) ................. 101 56 318

(51) Int. Cl.
*A47F 5/00* (2006.01)
(52) U.S. Cl. ................ 248/123.11; 248/162.1; 248/280.11
(58) Field of Classification Search ................ 464/185, 464/160; 74/89; 248/404, 123.11, 162.1, 248/406.1, 280.11, 123.2, 292.11, 297.11
See application file for complete search history.

(56) References Cited

U.S. PATENT DOCUMENTS

| | | | | |
|---|---|---|---|---|
| 3,848,463 A * | 11/1974 | Hejzlar et al. | ............ | 73/862.53 |
| 4,685,648 A * | 8/1987 | Dobner et al. | ............... | 248/572 |
| 5,213,293 A | 5/1993 | Muentener et al. | | |
| 5,395,304 A * | 3/1995 | Tarr et al. | ...................... | 602/26 |
| 5,492,296 A | 2/1996 | Biber | | |
| 5,575,764 A * | 11/1996 | Van Dyne | ..................... | 602/26 |
| 5,746,404 A * | 5/1998 | Merko | ................... | 248/123.11 |
| 6,070,839 A * | 6/2000 | Brenner et al. | ......... | 248/123.11 |
| 6,105,909 A * | 8/2000 | Wirth et al. | .............. | 248/123.2 |
| 6,523,796 B2 * | 2/2003 | Abramowsky et al. | ... | 248/284.1 |
| 6,732,988 B2 * | 5/2004 | Ihalainen et al. | ......... | 248/276.1 |
| 7,000,873 B2 * | 2/2006 | Metelski | ................ | 248/123.11 |
| 2004/0188578 A1 * | 9/2004 | Turner | ................... | 248/281.11 |

FOREIGN PATENT DOCUMENTS

DE 3444313 8/1985
DE 37 39 080 5/1989

* cited by examiner

*Primary Examiner*—Kimberly T Wood
(74) *Attorney, Agent, or Firm*—Walter Ottesen

(57) ABSTRACT

The invention relates to an arrangement for at least partially compensating a torque caused by gravitational forces acting on a mass body (2), which is rotatably supported on an axis of rotation (3). The arrangement includes a gas pressure spring (5) for providing a linear force. This linear force is transformed into a torque by means of a converter unit (7). The mass body (2) and the converter unit (7) can be coupled to each other in a way which allows for adjusting the amplitude and the phase of a compensating torque.

8 Claims, 6 Drawing Sheets

R5' < R5

ARRANGEMENT AND METHOD FOR AT LEAST PARTIALLY COMPENSATING A TORQUE CAUSED BY GRAVITATIONAL FORCES ACTING ON A MASS BODY

FIELD OF THE INVENTION

The invention relates to an arrangement for at least partially compensating for a torque caused by gravitational forces acting on a mass body which is rotatably supported on a holding unit. The invention further relates to a method for setting a torque balance state for a mass body which is rotatably supported on a holding unit.

BACKGROUND OF THE INVENTION

German patent publication 3,444,313 discloses a suspension mechanism for a surgical microscope. This suspension mechanism includes a spring for generating a linear force which compensates a torque caused by gravitational forces acting on the microscope. With a Bowden cable, the spring for generating the linear force is coupled to a gear wheel which is rigidly connected to the axis of rotation of the microscope. The suspension mechanism further includes adjusting means in the form of a gear shaft and a worm gear shaft which allow to adjust the amplitude and the phase of the compensating torque with respect to the torque caused by the gravitational forces.

From U.S. Pat. No. 5,492,296, a suspension mechanism for a surgical microscope is known, which comprises a spiral spring compensating a torque generated by gravitational forces. The force of the spiral spring can be set by an adjustment screw.

U.S. Pat. No. 5,213,293 discloses the use of gas pressure springs in a link-parallelogram for generating a force which counteracts the gravitational forces acting on a microscope stand.

SUMMARY OF THE INVENTION

It is an object of the invention to provide an arrangement for at least partially compensating a torque caused by gravitational forces acting on a surgical microscope which is rotatably supported on a stand unit thus allowing for a zero force movement of the surgical microscope about an axis of rotation which is at a distance from the center of mass of the surgical microscope. It is another object of the invention to provide a user friendly method of balancing a surgical microscope which is rotatably supported on a holding unit.

The above object is achieved by providing an arrangement for at least partially compensating a load-torque acting on a mass body which is rotatably supported on a holding unit. The arrangement includes: linear force generating means for generating a linear force; converter means for converting the linear force into a torque; and, a coupling unit which couples the converter means to the mass body. The coupling unit is adjustable to permit setting a torque transmitted from the converter means to the mass body. The coupling unit for transmitting a torque from the converter means to the mass body allows for coupling and decoupling of the converter means and the mass body. Preferably, the coupling unit allows not only for coupling and decoupling the mass body and the converter means but also for adjusting the phase of a torque acting on the converter means and the actual torque which is transmitted from the converter means to the mass body.

In particular, the arrangement of the invention provides a compensating torque which automatically has a correct phase position with respect to the torque caused by the gravitational forces acting on the center of mass of the mass body which is rotatably supported on the stand unit.

Preferably, the converter means include a crank mechanism to convert a linear force into a torque with only little friction.

In a preferred embodiment of the invention, the crank mechanism includes a crank member coupled to the linear force generating means, which has an arm of adjustable length. In varying the arm length of the crank member, the amplitude of a compensating torque as generated by the linear force generating means can be adjusted to a torque which is caused by gravitational forces.

Preferably, the crank mechanism in the arrangement comprises a threaded spindle for adjusting the arm length of the crank member. This allows setting the amplitude of a compensating torque in a very precise way.

Preferably, the arrangement of the invention further includes a latch mechanism for adjusting the phase of a compensating torque transmitted to the mass body. This allows for the transmission of relatively large torques from the converter means to the mass body.

Preferably, this latch mechanism includes a latch wheel having detent bores for accommodating a latch pin. This mechanism allows for little wear while coupling the converter means and the mass body.

Preferably, the latch mechanism further includes holding means for holding the latch pin and a slot for guiding the holding means, wherein movement of the holding means in the slot allows for coupling and decoupling of the mass body and the converter means. This allows for actuating the coupling means by setting the length of a crank arm in the converter means.

In another preferred embodiment of the invention, the coupling unit includes a threaded spindle meshing with a gear rim for adjusting the phase of a compensating torque transmitted to the mass body.

The linear force generating means can include a gas pressure spring. Such a gas pressure spring can provide push or pull forces. They allow for a relatively low weight of the arrangement while providing relatively high linear forces for the generation of compensating torques.

The method for setting a torque balance state of a mass body, which is rotatably supported on a stand unit, includes the steps of: decoupling the mass body from the converter means arranged for converting a linear force generated by a linear force generating means into a torque; allowing the mass body to be driven into a stable equilibrium state by gravity; allowing the converter means to be driven into an equilibrium state by the linear force generating means; and, coupling the mass body and the converter means in the stable equilibrium state of the mass body and the stable equilibrium state of the converter means. In this way, an equilibrium state for a surgical microscope can be set which is rotatably supported on a stand. By adjusting the length of a crank arm after coupling the mass body and the transformer means, very accurate compensation of the compensating torque and the torque caused by the gravitational forces acting on the mass body of a surgical microscope can be achieved.

BRIEF DESCRIPTION OF THE DRAWINGS

The invention will now be described with reference to the drawings wherein.

DESCRIPTION OF THE PREFERRED EMBODIMENTS OF THE INVENTION

Figure 1A:
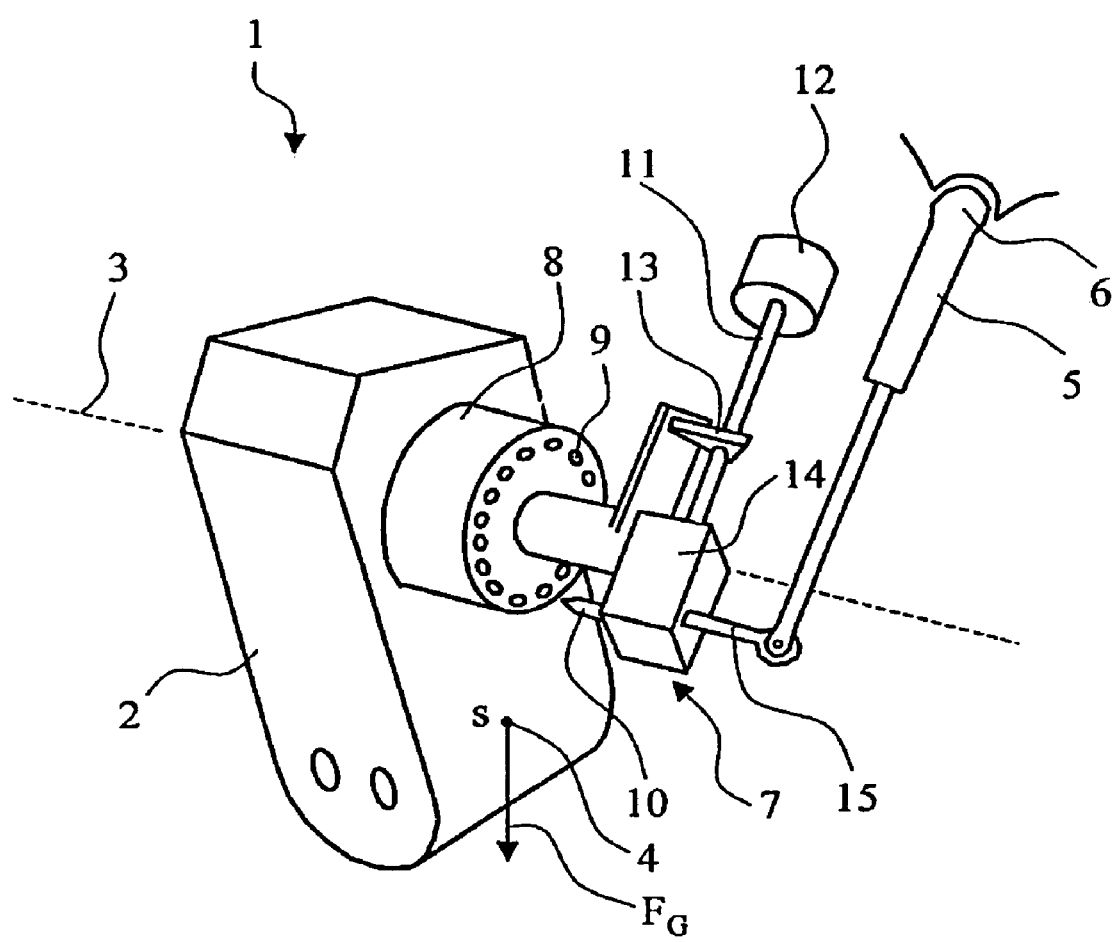
- FIG. 1a shows the arrangement of FIG. 1 in a decoupled configuration.
Figure 1B:
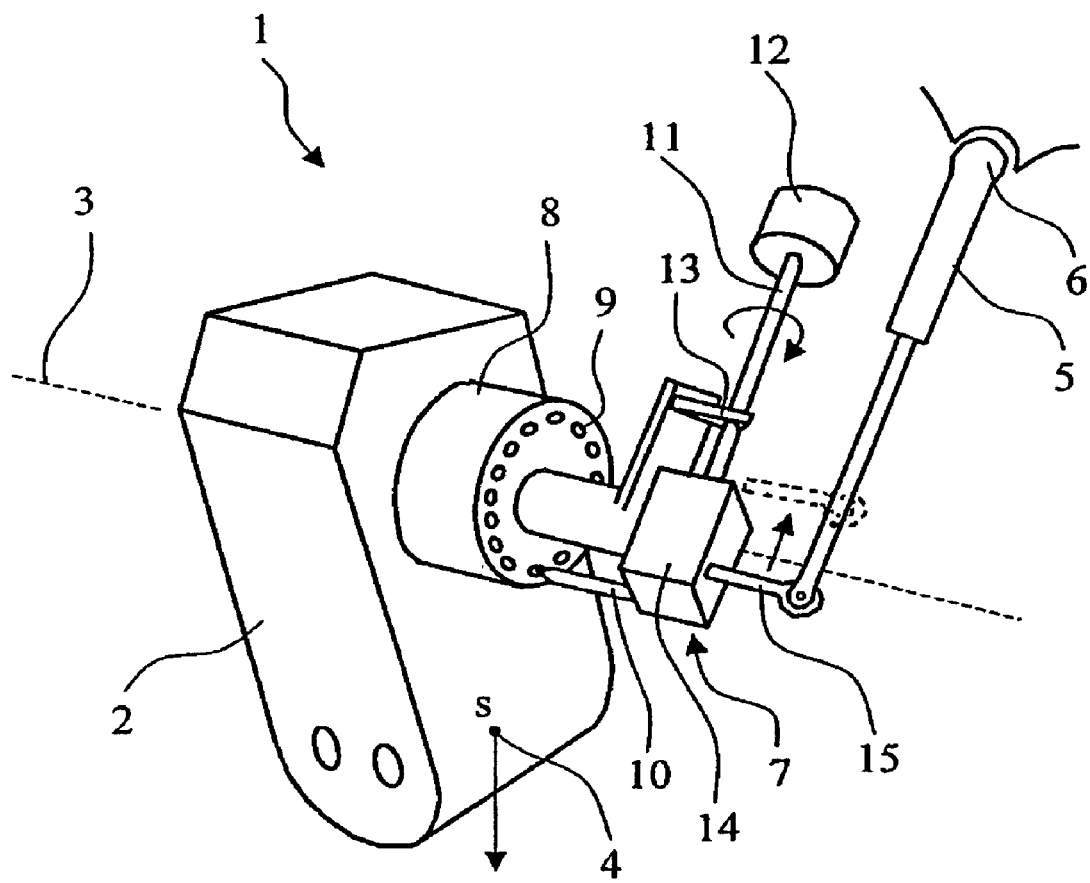
FIG. 1b shows the effect of the movement on the threaded spindle 11.
Figure 1:
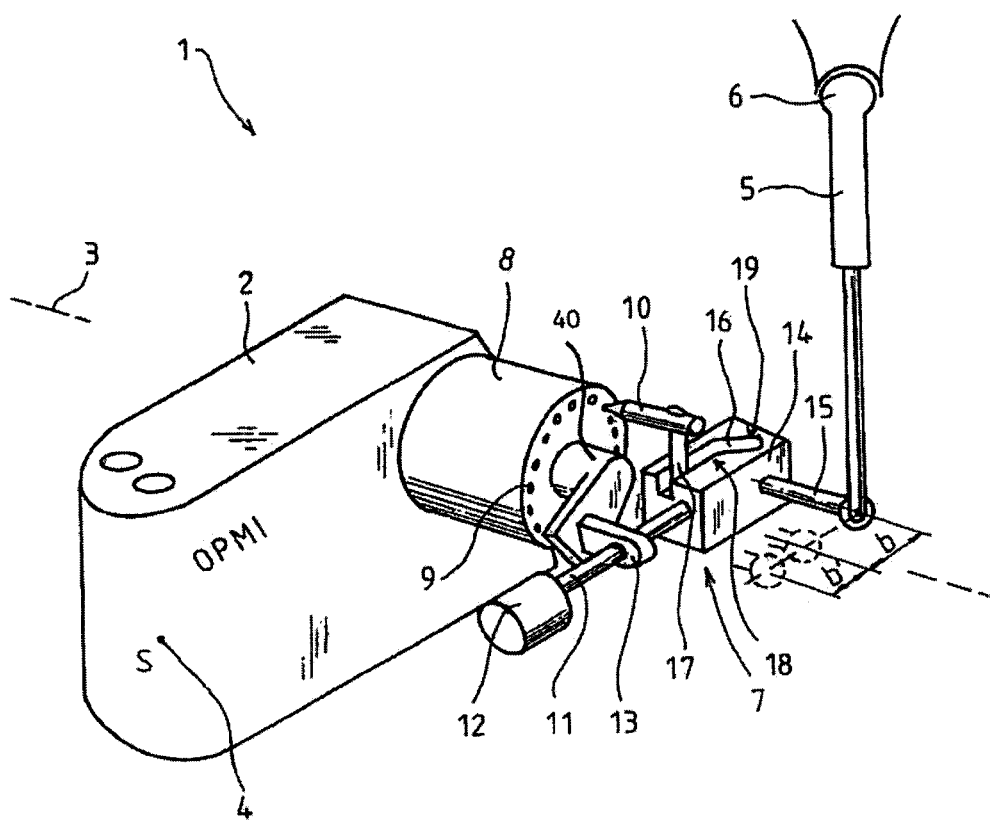
FIG. 1 shows a perspective view of a first arrangement for at least partially compensating a load-torque caused by gravi
Figure 1A:
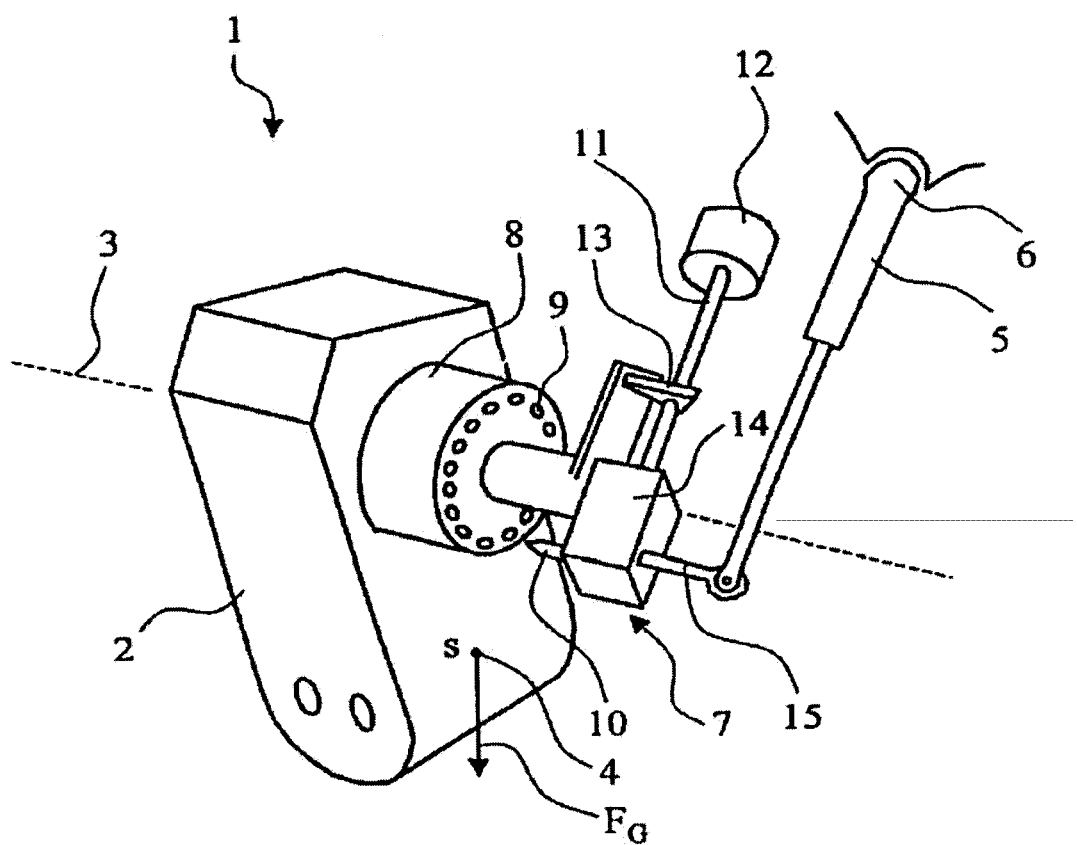
Figure 1B:
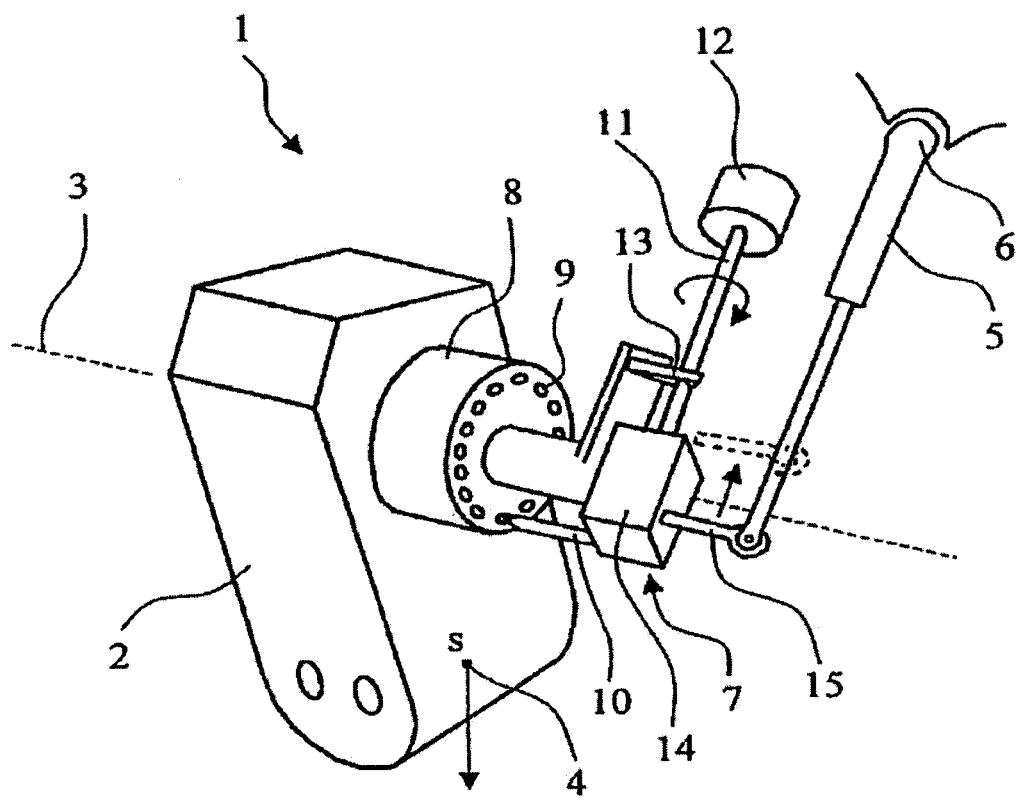
Figure 2:
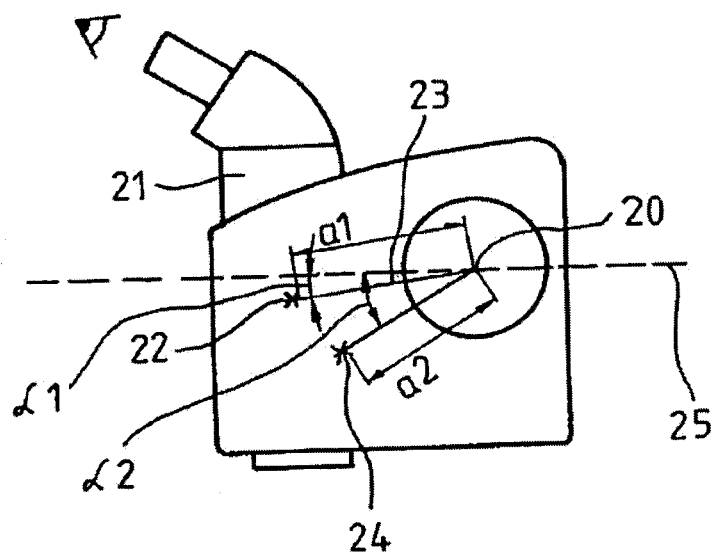
Figure 3:
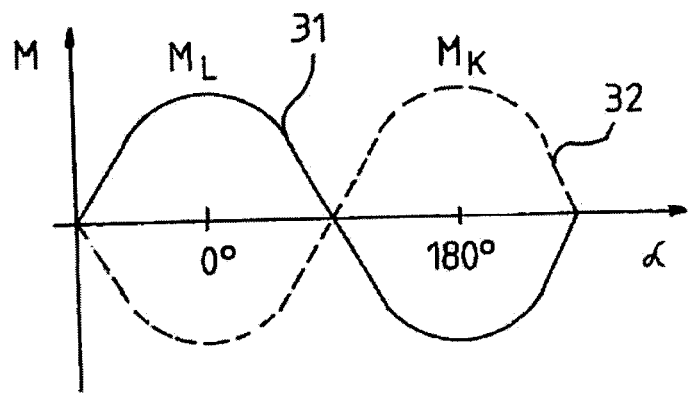
Figure 4:
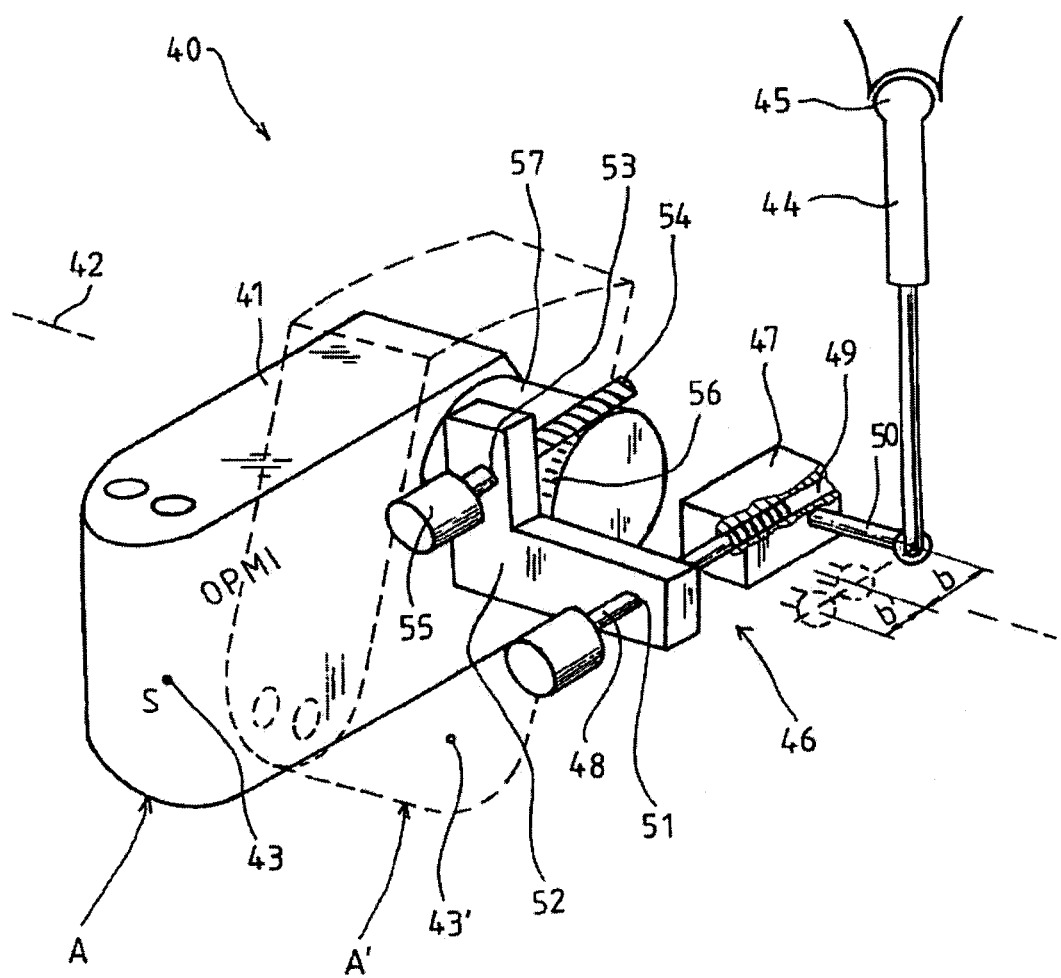
Figure 5A:
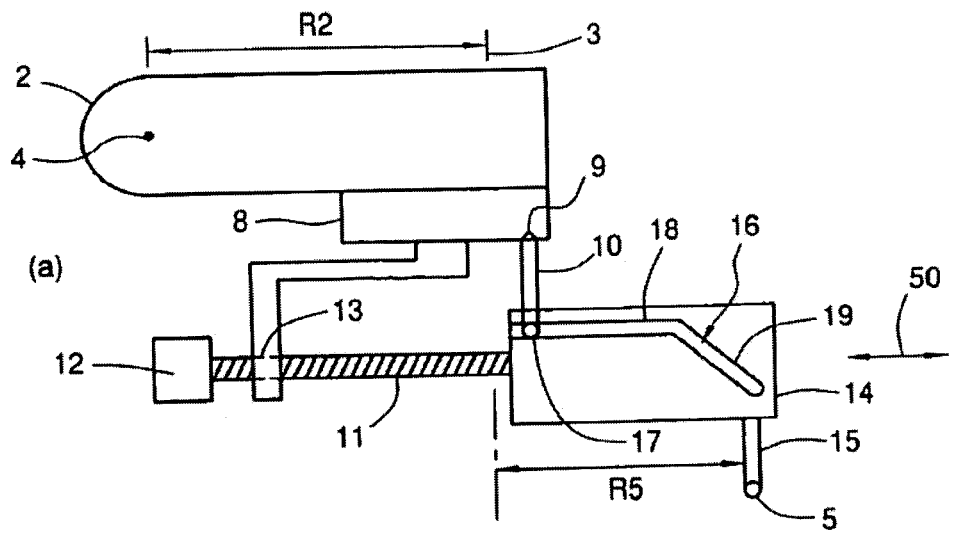
Figure 5B:
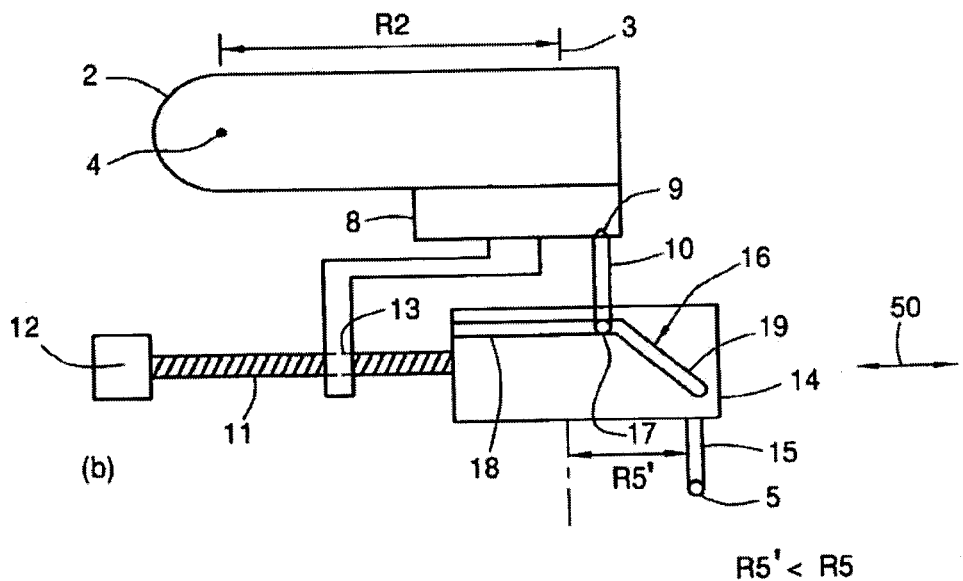
Figure 5C:
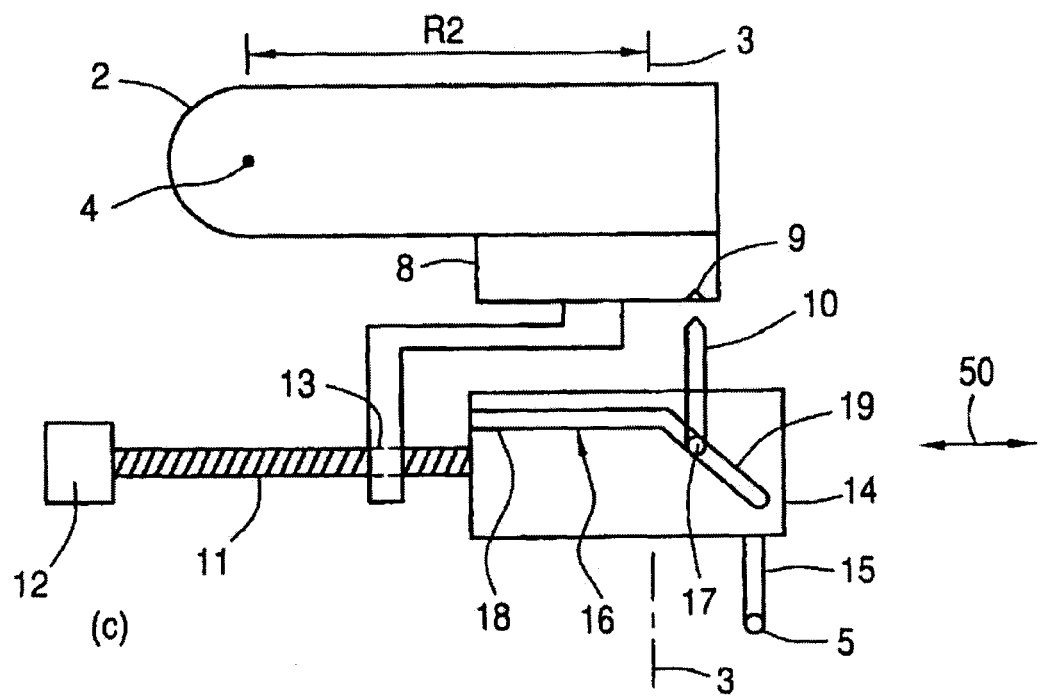

The arrangement for at least partially compensating a torque caused by gravitational forces includes a surgical microscope 2 which forms a mass body rotatably supported on a rotational axis 3 by a freewheel bearing (not shown). The surgical microscope 2 has a center of mass 4 located outside of the rotational axis 3. The location of the center of mass 4 is determined by the arrangement of the surgical microscope 2. This arrangement changes by attaching additional instruments, as for example, units allowing for co-observation or cameras. The gravitational force acts on the center of mass 4 of the surgical microscope 2 and generates a torque which tends to move the surgical microscope 2 into a stable equilibrium position. This stable equilibrium position corresponds to a location of the center of mass 4 of the surgical microscope 2 below the axis of the rotation 3 on the vertical perpendicular to this axis. In this position, the gravitational forces acting on the surgical microscope 2 cause zero torque. As shown in FIG. 1, the weight of the surgical microscope 2 acts at the center of mass S and generates a load torque about the axis of rotation 3 in the counterclockwise direction.

A gas pressure spring 5 is provided for compensating the torque generated by the gravitational forces in the arrangement 1. Instead of providing a gas pressure spring 5, a gas pull spring, a pull or pressure spring as, for example, a spiral spring or some other corresponding energy storing means could be used which allows for generating a linear force.

A ball and socket joint 6 bears the gas pressure spring 5 on a stand not shown in detail. The gas pressure spring 5 is connected to a converter unit 7 which transforms a linear force generated by the gas pressure spring 5 into a compensating torque. This compensating torque compensates a load-torque caused by the gravitational forces acting on the surgical microscope 2. The converter unit 7 includes a crank mechanism encompassing a slot stone 14 which is carried by a threaded spindle 11. This slot stone 14 has a connecting arm 15 which is connected to the gas pressure spring 5. The threaded spindle 11 and the slot stone 14 therefore act as a crank arm which tends to carry out a rotational movement about the axis of rotation 3 because of the linear force provided by the gas pressure spring 5. As shown in FIG. 1, the linear force applied by the spring 5 acts to the right of the rotational axis 3 and the converter unit defines a moment arm so that the torque generated by spring 5 acts in a clockwise direction or opposite to the counterclockwise direction of the load torque generated by the force of the weight of the microscope acting at the center of mass 4.

An adjustable coupling unit is provided for coupling the crank arm to the surgical microscope 2. This coupling unit includes a latch mechanism which encompasses a latch wheel 8 having bores 9. This latch wheel 8 is rigidly connected to the surgical microscope 2. In FIG. 1 and FIG. 1b, a latch pin 10 is shown engaging one of the bores 9. By means of this latch pin 10, a compensating torque generated by the gas pressure spring 5 is transmitted from the converter unit 7 to the surgical microscope 2. The effective length of the crank arm in the converter unit 7 can be adjusted by rotating the threaded spindle 11. For this, a turning knob 12 is provided on the threaded spindle 11 which permits rotating the threaded spindle 11 in a threaded bore 13 formed in lever arm structure 40. By rotating the threaded spindle 11 in the threaded bore 13, the position of the slot stone 14 and thus the effective length of the crank arm, which is acted upon by the spring force of the gas pressure spring 5 via the connecting arm 15, can be varied.

The latch pin 10 is held by a holding member 17 which is guided by the threaded spindle 11 via a guide slot 16 formed in the slot stone 14. By turning the threaded spindle 11, the slot stone 14 can be reciprocally moved in a direction perpendicular to the axis of rotation 3. By moving the slot stone 14, the position of the holding means 17 in the guide slot 16 is changed. Corresponding to the position of the slot stone 14, the effective length of the crank arm, which is exposed to the force of the gas pressure spring 5, is varied and correspondingly different compensating torques are generated.

The guide slot 16 in the slot stone 14 includes a first section 18, where the guide slot 16 is perpendicular to the axis of rotation 3. In a second section 19, the guide slot 16 follows a direction forming an angle with respect to the rotational axis 3. By varying the position of the slot stone, the holding member 17, with the latch pin 10 attached thereto, is moved in the guide slot 16 in the direction of the axis of rotation 3. In this way, the latch pin 10 is coupled to the latch wheel 8 or decoupled therefrom. FIG. 1a shows a position the surgical microscope 2 assumes when the latch pin 10 is decoupled from the latch wheel 8.

Figure 5A:
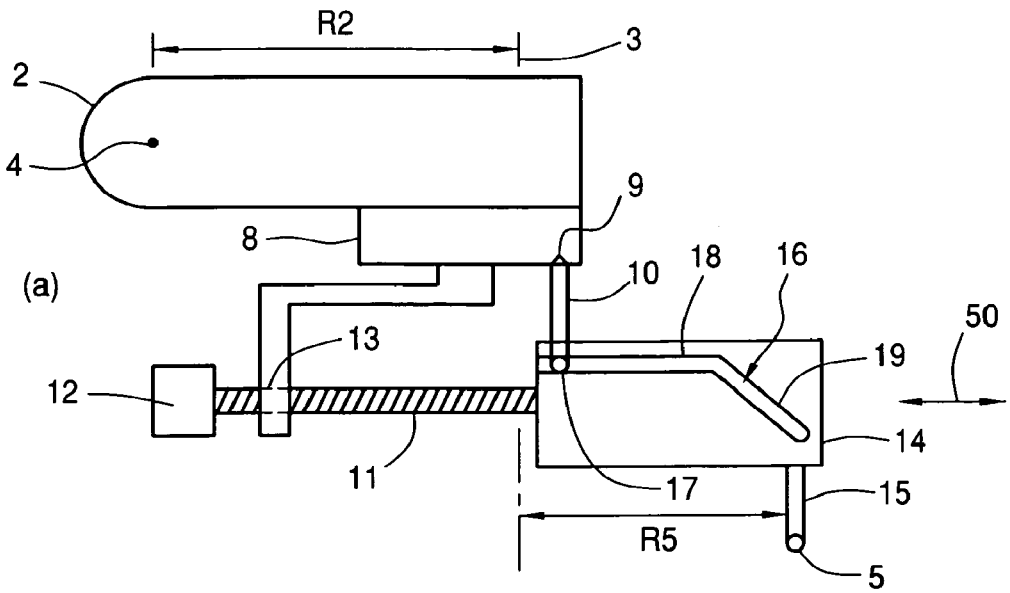
FIG. 5a is a plan showing the slot stone of the converter unit in a first position whereat the compensating moment arm R5 is as shown.

Referring to FIG. 5a, it can be seen that the latch pin 10 is seated in the detent bore 9 of the latch wheel 8 which is fixedly attached to the surgical microscope 2. The load on the surgical microscope acts at the center of mass 4 and generates a load torque about the rotational axis 3 in a clockwise direction with the moment arm of this torque being identified by reference character R2.

Assuming that an operator wishes to adjust the compensating torque generated by the force of pressure spring 5 to balance the load torque because of a load change on the surgical microscope 2, for example, because an accessory such as a camera has been mounted thereon. The operator would then rotate knob 12 so that the threaded spindle 11 rotates in the threaded bore 13 in the holding arm structure 40 shown in FIG. 1 thereby moving the slot stone 14 in a direction 50 perpendicular to the rotational axis 3. The slot stone 14 is moved to the left from the position shown in FIG. 5a and is then in the position shown in FIG. 5b. With this action, the operator has shortened the moment arm as shown in FIG. 5b (R5'<R5) and adjusted the compensating torque which acts in the clockwise direction about axis 3 to balance the new load torque acting in the counterclockwise direction about axis 3.

The holding member 17 has not moved in the first section 18 of guide slot 16; instead, the slot stone 14 has moved to the left relative to the holding member 17 thereby adjusting the compensating torque by shortening the length of the moment arm to R5'.

By turning the threaded spindle 11, the slot stone 14 is reciprocally moved in a direction perpendicular to the axis of rotation 3. By moving the slot stone 14, the position of the holding member 17 in the guide slot 16 is changed.

Figure 5B:
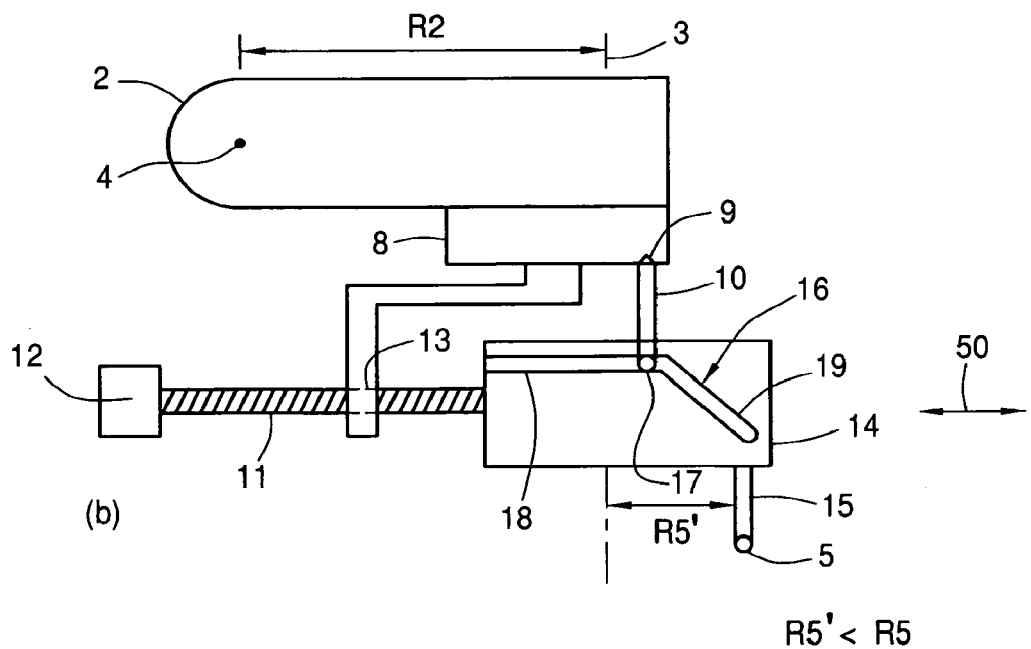
FIG. 5b is a view corresponding to FIG. 5a except that the slot stone has been shifted to the left to shorten the length of the compensating torque arm which is here identified as R5'; and, FIG. 5c shows the arrangement of FIGS. 5a and 5b wherein the slot stone has been moved so far to the left that the holding member is now in the angled second section of the guide slot and the latch pin is withdrawn from the detent bore.
Figure 5C:
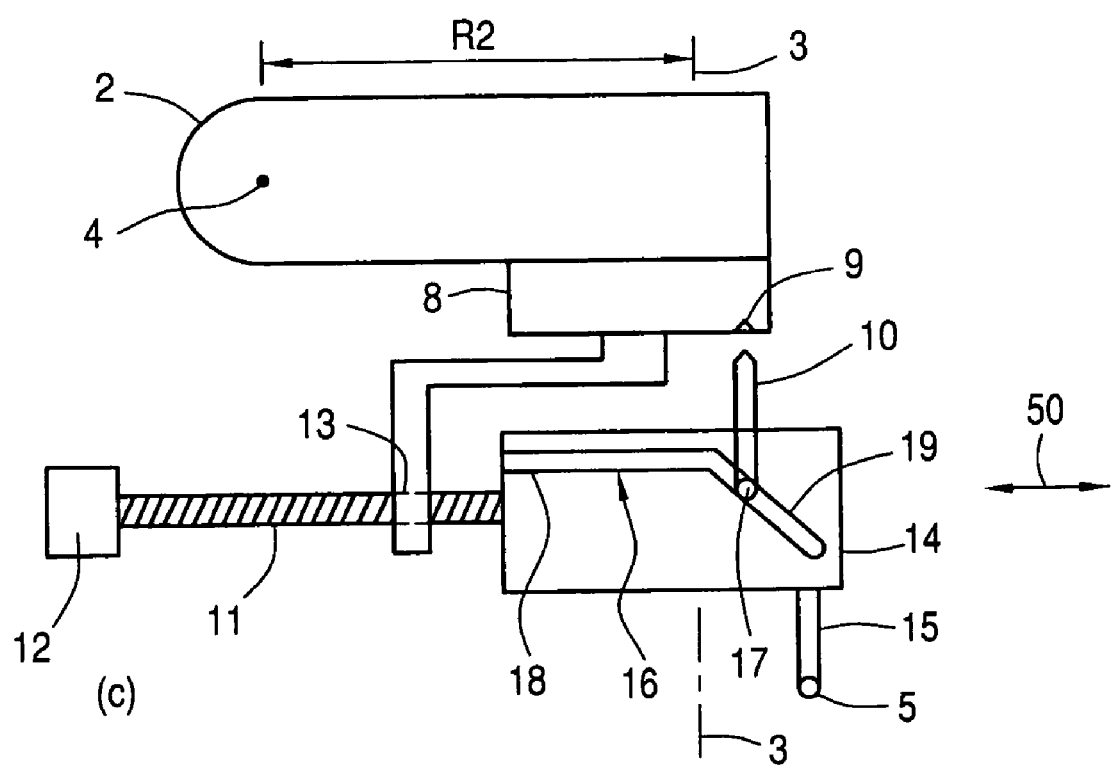

The slot stone 14 can be moved reciprocally as indicated by the double arrow 50 in each of FIGS. 5a to 5c thereby changing the position or location of holding member 17 in the guide slot 16. This direction 50 is perpendicular to the rotational axis 3.

By changing the position of the slot stone 14 relative to the holding member 17 and latch pin 10, the moment arm of the compensating torque supplied by the pressure spring 5 can be changed.

Corresponding to the position of the slot stone 14, the effective length of the crank arm (moment arm R5 or R5'), which is exposed to the force of the gas pressure spring 5, is varied and correspondingly different compensating torques are generated.

The length of the moment arm of the compensating torque is changed by moving the slot stone 14 with this movement being relative to the holding member 17. As a consequence of this relative movement, the position of holding member 17 is changed in the guide slot 16 even though the holding member 17 has not moved in FIGS. 5a and 5b where it is shown in the first section 18 of the guide slot 16.

FIG. 5c shows the slot stone 14 moved even farther to the left in one of the two reciprocal directions 50 perpendicular to the rotational axis 3 so that now the latch pin 10 has been pulled from the detent bore 9 by the second section 19 of the guide slot 16 in a direction parallel to the rotational axis 3.

The guide slot 16 in the slot stone 14 includes the first section 18, where the guide slot 16 is perpendicular to the axis of rotation 3. In the second section 19, the guide slot 16 follows a direction forming an angle with respect to the rotational axis 3. When the slot stone 14 is moved so far to the left as shown in FIG. 5c, the holding member 17 enters the second section 19 of guide slot 16 whereat the side wall of the second section 19 acts as a cam to move the holding member 17 with the latch pin 10 in the direction of the rotational axis 3. In this way, the latch pin 10 is coupled to the latch wheel 8 or decoupled therefrom.

When the microscope is in the position shown in FIG. 1a, the threaded spindle 11 may, as indicated by the circular arrow in FIG. 1b, be turned so that the slot stone 14 including the connecting arm 15 is moved in the general direction of the straight arrow. Movement into the general direction of the straight arrow will lead to an engagement of the latch pin 10 with the suitable bore 9 of the latch wheel 8. This engagement, in turn, results in an effective connection between the surgical microscope 2 and the converter unit 7. After this effective connection has been established and through adjustment of the threaded spindle 11, the connecting arm 15 may be moved through the rotational axis 3 around which the surgical microscope is pivotable (see phantom outline of connecting arm 15). This allows an adjustment of the phase and amplitude via the gas pressure spring 5 to compensate for the torque exerted on the surgical microscope 2. Thus, by changing the position of the slot stone 14 and by appropriately choosing the bore in the latch wheel 8 in which the latch pin 10 is accommodated, a compensating torque, which is generated by the gas pressure spring 5, can be adapted in phase and amplitude to a given load torque generated by gravitational forces acting at the center of mass 4. FIG. 1 shows a position of the surgical microscope in which torque compensation has been achieved.

Figure 2:
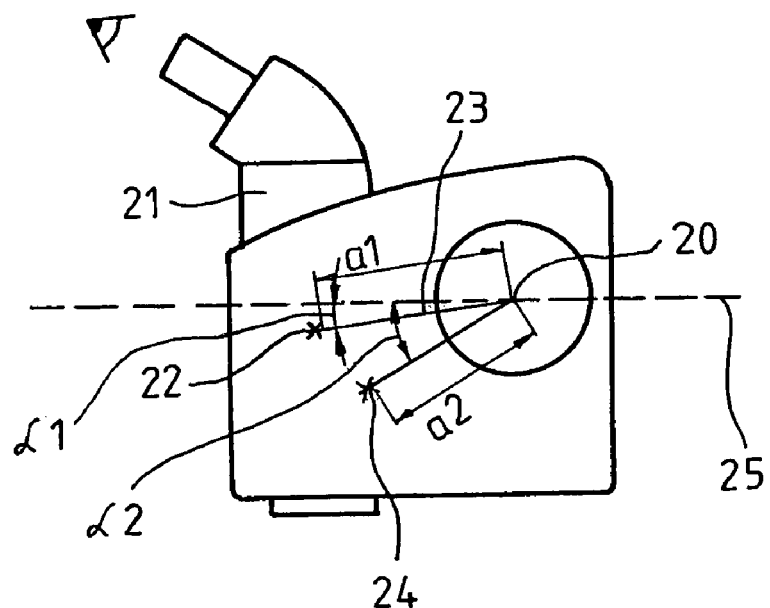
FIG. 2 shows a side view of a surgical microscope supported on a rotational axis.

FIG. 2 illustrates the relationship between a shift of the center of mass and the corresponding change in torque generated by gravitational forces for the surgical microscope 21 supported on an axis of rotation 20. The surgical microscope 21 has a center of mass having position 22. The gravitational force acting at the center of mass acts on the axis of rotation 20 with a lever arm 23 of length $a_1$ and generates a load-torque $M_{L1}$ about this axis. If additional instruments are provided on the surgical microscope 21, as for example a video camera, additional lenses or modules attached in front of the main objective lens, the center of mass is shifted from position 22 to position 24. The change in the total mass of the surgical microscope system and the inherent shift of the center of mass give rise to a corresponding change of the torque as generated by gravity.

For the surgical microscope 21 of FIG. 2, the load-torque $M_{L1}$, caused by gravity of the system with the center of mass at position 22, is given by:

$$M_{L_1} = m_1 g a_1 \cos(\alpha_1),$$

wherein:

$m_1$ is the total mass of the surgical microscope with the center of mass at position 22, g is the gravitational constant, $a_1$ is the distance of the center of mass of the surgical microscope at position 22 from the axis of rotation 20, and $\alpha_1$ is the angle between the line connecting the center of mass 22 and the axis of rotation 20 and the horizontal line 25.

When attaching additional instruments, the total mass of the surgical microscope is changed from $m_1$ to $m_2$. At the same time, the center of mass of the surgical microscope is shifted from position 22 to position 24. In this case, the load-torque $M_{L2}$ generated by the gravitational forces is:

$$M_{L_2} = m_2 g a_2 \cos(\alpha_2),$$

wherein:

$m_2$ is the total mass of the surgical microscope with the center of mass in position 24;

g is the gravitational constant;

$a_2$ is the distance of the center of mass of the surgical microscope at position 24 from the axis of rotation 20; and, $\alpha_2$ is the angle between the line connecting the center of mass and the axis of rotation 20 and the horizontal line 23.

A change in the total mass of the surgical microscope and a shift of its center of mass changes, in general, the torque which arises at the axis of rotation 20. In order to allow a zero force movement of the surgical microscope system about the axis of rotation 20, a corresponding adaptation of the phase and amplitude of the compensating torque is required.

Figure 3:
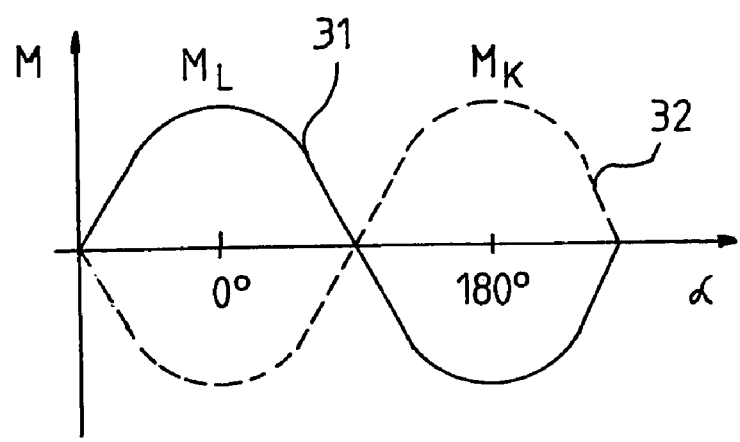
FIG. 3 illustrates the phase shift of the load-torque caused by gravitational forces and the compensating torque for torque compensation.

FIG. 3 shows with curve 31 a dependence of the load-torque $M_L$ caused by gravity on the angular position $\alpha$ of a surgical microscope on an axis of rotation. For complete compensation of this torque, a compensating torque $M_K$ is required having a phase and amplitude which is adapted to the torque $M_L$ such that the compensating torque $M_K$ and the torque $M_L$ cancel each other. If the compensating torque $M_K$ at the surgical microscope follows the curve 32, the surgical microscope is in equilibrium irrespective of its angular position with respect to its axis of rotation on which it is supported. In this way, it is possible to move the surgical microscope about this axis of rotation at virtually zero force.

In the following it will be described with reference to FIG. 1, how, for a given torque $M_L$ caused by gravity, a corresponding compensating torque $M_K$ can be set. For this, in a first step, the surgical microscope 2 is decoupled from the converter unit 7 and the gas pressure spring 5 by opening the latch mechanism. As a consequence thereof, the surgical microscope tilts under the action of gravity about the axis of rotation 3 and moves into a stable equilibrium position. In this stable equilibrium position, the center of mass 4 of the system is on the vertical perpendicular to the axis of rotation 3. At the same time, the converter unit 7 is driven into stable equilibrium position by the gas pressure spring 5, in which the spring arm of the gas pressure spring 5 and the crank arm of the converter unit 7 (formed by the slot stone 14 and the threaded spindle 11) are aligned parallel to each other. When the latching unit is closed in these mutually corresponding stable equilibrium positions of the surgical microscope 2 and the converter unit 7 with the gas pressure spring 5, then the load-torque $M_L$ caused by the surgical microscope 2 and the compensating torque $M_K$ generated by the gas pressure spring 5 are shifted in phase by 180°. By rotating the threaded spindle 11, the effective length of the crank arm in the converter unit 7 is then set so that the amplitude of this compensating torque $M_K$ is adapted to the amplitude of the load-torque $M_L$ generated by gravity. The result is a complete torque balance for the surgical microscope 2 on the axis of rotation 3 irrespective of angular position.

Figure 4:
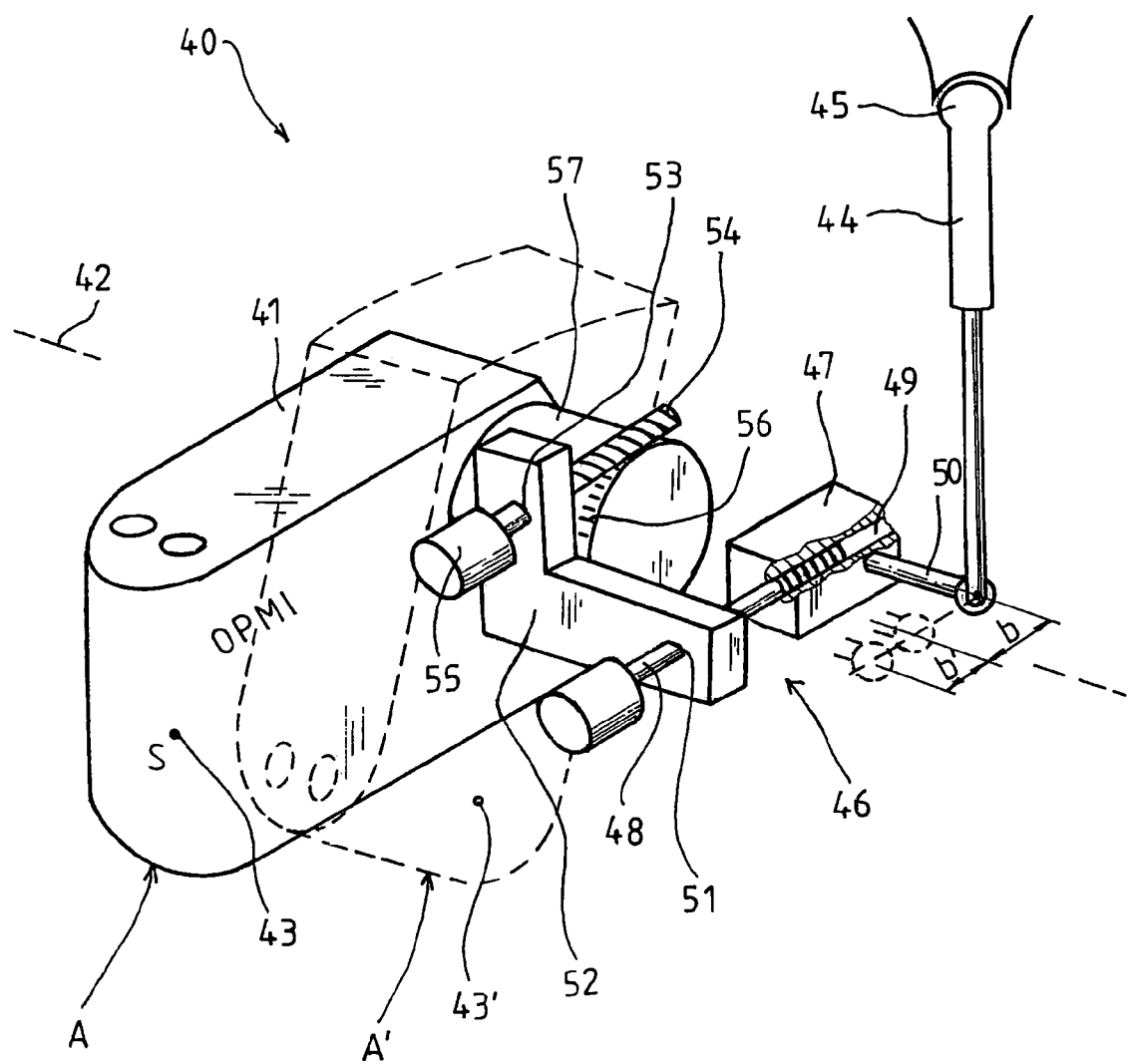
FIG. 4 shows a perspective view of a second embodiment of an arrangement for at least partially compensating a load-torque.

FIG. 4 shows another embodiment 40 of an arrangement for at least partially compensating a torque as an alternative to the arrangement presented in FIG. 1. The arrangement 40 encompasses a surgical microscope 41 defining a mass unit supported on an axis of rotation 42 by a freewheel bearing (not shown). In position A, the surgical microscope 41 has a center of mass which lies outside the axis of rotation 42 at a location 43. As shown in the arrangement 1 presented in FIG. 1, the position of the center of mass of the arrangement 40 is determined by the mass distribution of the surgical microscope 41 and additional instruments which are attached to it. The gravitational force acting on the center of mass of the surgical microscope 41 generates a load-torque which tends to move the surgical microscope 41 from a position A into a stable equilibrium position. This stable equilibrium position corresponds to a position A' of the surgical microscope shown in phantom outline with the center of mass 43' lying below the axis of rotation 42 on a vertical line perpendicular to axis 42. In this position, the gravitational forces acting on the surgical microscope 41 generate no torque on the instrument.

For compensating the load-torque, the arrangement 40 includes a gas pressure spring 44, which may be used for generating a linear force. The spring 44 could also be a gas tension spring, a tension or pressure spring formed as a helical spring or some other corresponding energy storing means.

The gas pressure spring 44 is rotatably connected to a stand unit by a ball joint 45. This gas pressure spring 44 is connected to a converter unit 46 configured as a crank mechanism, which converts a linear force provided by the gas pressure spring 44 into a compensating torque. Similar to the converter unit 7 shown in FIG. 1, this crank mechanism includes a crank block 47 and a threaded spindle 48 which is guided in a threaded bore 49 of the crank block 47. The gas pressure spring 44 acts on the crank block 47 via a connecting arm 50. The threaded spindle 48 has a turning knob and is rotatably journalled in a bearing 51 in unit 52.

The threaded spindle 48 and the crank block 47 conjointly define a crank arm which tends to carry out a rotation movement about the axis of rotation 42 under the linear force provided by the gas pressure spring 44. By rotating the threaded spindle 48, the length of this crank arm can be adjusted.

The compensating torque provided by the converter unit is conducted to the surgical microscope 41 via an adjustable coupling unit where it balances the torque generated by gravitational forces on the surgical microscope 41. The coupling unit is in the form of a worm gear. For this, a worm gear 54 is provided which is journalled in another bearing 43 on the unit 52. The worm gear 54 can be rotated by a turning knob 55. The worm gear 54 meshes with a rim gear or pinion 56 provided on a connecting wheel 57 which is fixedly connected to the surgical microscope 41. This connecting wheel 57 transmits a compensating torque to the surgical microscope 41, which is generated by the gas pressure spring 44 and the crank block 47 with the threaded spindle 48. By turning the worm gear 54, the surgical microscope 41 is tilted about the axis of rotation 42. In this way, it is possible to adjust the phase position of a compensating torque with respect to a torque caused by gravitational forces acting on the surgical microscope 41 in a very precise way.

It is understood that the foregoing description is that of the preferred embodiments of the invention and that various changes and modifications may be made thereto without departing from the spirit and scope of the invention as defined in the appended claims.

What is claimed is:

1. An arrangement for at least partially compensating a load torque acting on a mass body which is supported on a stand unit so as to be rotatable about an axis of rotation in a first direction as a consequence of said load torque, said arrangement comprising:

force means for generating a linear force;

a converter unit connected to said force means and being for converting said linear force into a compensating torque to counter said load torque;

said converter unit defining a moment arm between said linear force and said axis for said compensating torque and said converter unit including an adjusting device for adjusting the length of said moment arm to adjust said compensating torque to a magnitude needed to balance said load torque;

an adjustable coupling unit for transmitting said compensating torque between said converter unit and said mass body so as to cause said compensating torque to act in a second direction about said axis of rotation opposite to said first direction to balance said load torque; and, said coupling unit including a latch mechanism for adjusting the phase of a compensating torque transmitted to the mass body.

2. The arrangement of claim 1, wherein said linear force generating means comprises a gas pressure spring arranged for providing thrust forces.

3. The arrangement of claim 1, wherein said linear force generating means comprises a gas pressure spring arranged for providing pull forces.

4. The arrangement of claim 1, wherein said mass body is a surgical microscope.

5. An arrangement for at least partially compensating a load torque acting on a mass body which is rotatably supported on a stand unit about an axis of rotation in a first direction as a consequence of said load torque, said arrangement comprising:

force means for generating a linear force;

a converter unit connected to said force means and being for converting said linear force into a compensating torque to counter said load torque;

said converter unit defining a moment arm between said linear force and said axis for said compensating torque and said converter unit including an adjusting device for adjusting the length of said moment arm;

an adjustable coupling unit for transmitting said compensating torque between said converter unit and said mass body so as to cause said compensating torque to act in a second direction about said axis of rotation opposite to said first direction to balance said load torque;

said coupling unit including a latch mechanism for adjusting the phase of said compensating torque transmitted to the mass body; and, said latch mechanism including a latch pin and a latch wheel attached to said mass body and said latch wheel having detent bores for accommodating said latch pin therein.

6. The arrangement of claim 5, wherein said latch mechanism further includes: a holding member for holding said latch pin; and, a slot for guiding said holding member so that a movement of said holding member in said slot allows for coupling and decoupling said latch pin with respect to said detent bores.

7. An arrangement for at least partially compensating a load torque acting on a mass body which is supported on a stand unit so as to be rotatable about an axis of rotation in a first direction as a consequence of said load torque, said arrangement comprising:

force means for generating a linear force;

a converter unit connected to said force means and being for converting said linear force into a compensating torque to counter said load torque;

said converter unit defining a moment arm between said linear force and said axis for said compensating torque and said converter unit including an adjusting device for adjusting the length of said moment arm to adjust said compensating torque to a magnitude needed to balance said load torque;

an adjustable coupling unit for transmitting said compensating torque between said converter unit and said mass body so as to cause said compensating torque to act in a second direction about said axis of rotation opposite to said first direction to balance said load torque; and, said converter unit and said adjusting device thereof being configured as a crank mechanism.

8. The arrangement of claim 7, wherein said crank mechanism comprises: a slot stone connected to said force means; a lever connected to said mass body and defining a threaded bore; a threaded spindle threadably engaging said threaded bore and being connected to said slot stone; and, said threaded spindle being rotatable in said threaded bore for adjusting the length of said moment arm.

* * * * *

UNITED STATES PATENT AND TRADEMARK OFFICE
CERTIFICATE OF CORRECTION

| | | |
|---|---|---|
| PATENT NO. | : 7,641,155 B2 | Page 1 of 9 |
| APPLICATION NO. | : 10/298554 | |
| DATED | : January 5, 2010 | |
| INVENTOR(S) | : Hartmut Gaertner et al. | |

It is certified that error appears in the above-identified patent and that said Letters Patent is hereby corrected as shown below:

Title page, "8 Claims, 6 Drawings Sheets" is changed to reflect --8 Claims, 7 Drawing Sheets --.

In the Drawings

The drawing sheets 1-6 of 6 consisting of Fig(s) 1A-5C should be deleted and substitute therefore the attached drawing sheets 1-7 of 7 consisting of Fig(s) 1-5C.

Signed and Sealed this
Fifth Day of July, 2011

David J. Kappos
*Director of the United States Patent and Trademark Office*

(12) United States Patent
Gaertner et al.

(10) Patent No.: US 7,641,155 B2
(45) Date of Patent: Jan. 5, 2010

(54) ARRANGEMENT AND METHOD FOR AT LEAST PARTIALLY COMPENSATING A TORQUE CAUSED BY GRAVITATIONAL FORCES ACTING ON A MASS BODY

(75) Inventors: Hartmut Gaertner, Oberkochen (DE); Fritz Zimmermann, Essingen (DE); Wolfgang Strauss, Staig (DE)

(73) Assignee: Carl-Zeiss-Stiftung, Oberkochen (DE)

(*) Notice: Subject to any disclaimer, the term of this patent is extended or adjusted under 35 U.S.C. 154(b) by 0 days.

(21) Appl. No.: 10/298,554

(22) Filed: Nov. 19, 2002

(65) Prior Publication Data
US 2003/0094549 A1    May 22, 2003

(30) Foreign Application Priority Data
Nov. 19, 2001  (DE) ............................ 101 56 318

(51) Int. Cl.
*A47F 5/00* (2006.01)
(52) U.S. Cl. .............................. 248/123.11; 248/162.1; 248/280.11
(58) Field of Classification Search .............. 464/185, 464/160; 74/89; 248/404, 123.11, 162.1, 248/406.1, 280.11, 123.2, 292.11, 297.11
See application file for complete search history.

(56) References Cited

U.S. PATENT DOCUMENTS

| | | | | |
|---|---|---|---|---|
| 3,848,463 A * | 11/1974 | Hejzlar et al. | ............ | 73/862.53 |
| 4,685,648 A * | 8/1987 | Dobner et al. | ............ | 248/572 |
| 5,213,293 A | 5/1993 | Muentener et al. | | |
| 5,395,304 A * | 3/1995 | Tarr et al. | ............ | 602/26 |
| 5,492,296 A | 2/1996 | Biber | | |
| 5,575,764 A * | 11/1996 | Van Dyne | ............ | 602/26 |
| 5,746,404 A * | 5/1998 | Merko | ............ | 248/123.11 |
| 6,070,839 A * | 6/2000 | Brenner et al. | ............ | 248/123.11 |
| 6,105,909 A * | 8/2000 | Wirth et al. | ............ | 248/123.2 |
| 6,523,796 B2 * | 2/2003 | Abramowsky et al. | ... | 248/284.1 |
| 6,732,988 B2 * | 5/2004 | Ihalainen et al. | ........ | 248/276.1 |
| 7,000,873 B2 * | 2/2006 | Metelski | ............ | 248/123.11 |
| 2004/0188578 A1* | 9/2004 | Turner | ............ | 248/281.11 |

FOREIGN PATENT DOCUMENTS

| | | |
|---|---|---|
| DE | 3444313 | 8/1985 |
| DE | 37 39 080 | 5/1989 |

* cited by examiner

*Primary Examiner*—Kimberly T Wood
(74) *Attorney, Agent, or Firm*—Walter Ottesen

(57) ABSTRACT

The invention relates to an arrangement for at least partially compensating a torque caused by gravitational forces acting on a mass body (2), which is rotatably supported on an axis of rotation (3). The arrangement includes a gas pressure spring (5) for providing a linear force. This linear force is transformed into a torque by means of a converter unit (7). The mass body (2) and the converter unit (7) can be coupled to each other in a way which allows for adjusting the amplitude and the phase of a compensating torque.

8 Claims, 7 Drawing Sheets

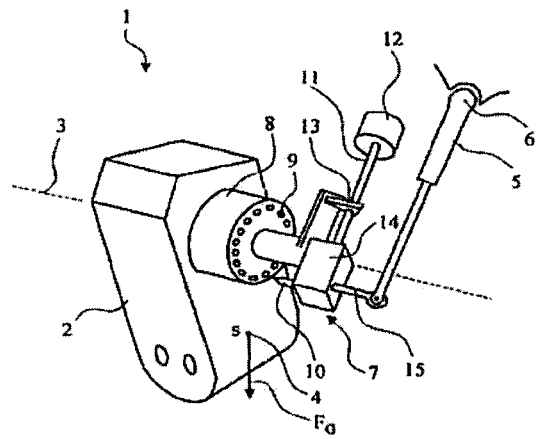

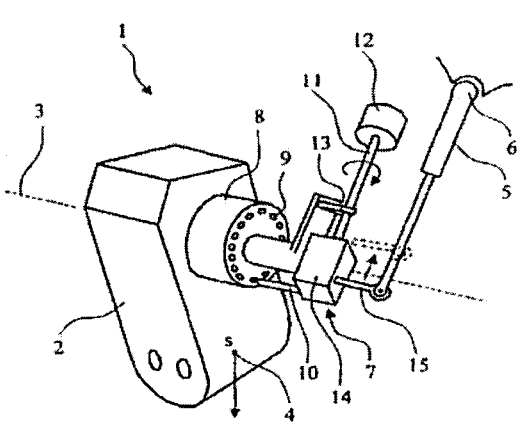

R5' < R5